US010134148B2

United States Patent
Heine et al.

(10) Patent No.: US 10,134,148 B2
(45) Date of Patent: Nov. 20, 2018

(54) METHOD OF ASSESSING BREAST DENSITY FOR BREAST CANCER RISK APPLICATIONS

(71) Applicant: H. LEE MOFFITT CANCER CENTER AND RESEARCH INSTITUTE, INC., Tampa, FL (US)

(72) Inventors: John J. Heine, New Port Richey, FL (US); Thomas A. Sellers, Tampa, FL (US); Erin E. Fowler, Tampa, FL (US)

(73) Assignees: H. Lee Moffitt Cancer Center and Research Institute, Inc., Tampa, FL (US); Mayo Foundation for Medical Education and Research, Rochester, MN (US)

( * ) Notice: Subject to any disclaimer, the term of this patent is extended or adjusted under 35 U.S.C. 154(b) by 179 days.

(21) Appl. No.: 14/893,632

(22) PCT Filed: May 30, 2014

(86) PCT No.: PCT/US2014/040169
§ 371 (c)(1),
(2) Date: Nov. 24, 2015

(87) PCT Pub. No.: WO2014/194171
PCT Pub. Date: Dec. 4, 2014

(65) Prior Publication Data
US 2016/0117843 A1 Apr. 28, 2016

Related U.S. Application Data

(60) Provisional application No. 61/828,778, filed on May 30, 2013.

(51) Int. Cl.
*G06K 9/00* (2006.01)
*G06T 7/40* (2017.01)
(Continued)

(52) U.S. Cl.
CPC .............. *G06T 7/403* (2013.01); *A61B 6/502* (2013.01); *A61B 6/5217* (2013.01); *G06T 5/40* (2013.01);
(Continued)

(58) Field of Classification Search
CPC ........... G06T 7/44; G06T 5/40; G06T 7/0014; G06T 7/403; A61B 6/502; A61B 6/5217
(Continued)

(56) References Cited

U.S. PATENT DOCUMENTS

| 6,282,305 | B1 * | 8/2001 | Huo | G06T 7/0012 |
| | | | | 382/128 |
| 2003/0174873 | A1 * | 9/2003 | Giger | G06K 9/3233 |
| | | | | 382/128 |
| 2009/0232376 | A1 * | 9/2009 | Raundahl | G06K 9/527 |
| | | | | 382/131 |

OTHER PUBLICATIONS

Heine, J.J., et al., "Full field digital mammography and breast density: comparison of calibrated and non-calibrated measurements"; Acad Radiol, vol. 18, No. 11; 2011; pp. 1430-1436.*
(Continued)

*Primary Examiner* — Van D Huynh
(74) *Attorney, Agent, or Firm* — Meunier Carlin & Curfman

(57) ABSTRACT

Breast density is a significant breast cancer risk factor measured from mammograms. Disclosed is a methodology for converting continuous measurements of breast density and calibrated mammograms into a four-state ordinal variable approximating the BI-RADS ratings. In particular, the present disclosure is directed to a calibration system for a specific full field digital mammography (FFDM) technology. The calibration adjusts for the x-ray acquisition technique differences across mammograms resulting in standardized images. The approach produced various calibrated and validated measures of breast density, one of which
(Continued)

assesses variation in the mammogram referred to as Vc (i.e. variation measured from calibrated mammograms). The variation in raw mammograms [i.e. Vr] is a valid breast density risk factor in both FFDM in digitized film mammograms.

18 Claims, 2 Drawing Sheets

(51) Int. Cl.
    *A61B 6/00*      (2006.01)
    *G06T 5/40*      (2006.01)
    *G06T 7/00*      (2017.01)
    *G06T 7/44*      (2017.01)

(52) U.S. Cl.
    CPC .............. *G06T 7/0014* (2013.01); *G06T 7/44* (2017.01); *A61B 6/5205* (2013.01); *A61B 6/583* (2013.01); *G06T 2207/10116* (2013.01); *G06T 2207/30068* (2013.01)

(58) Field of Classification Search
    USPC .......................................................... 382/132
    See application file for complete search history.

(56) References Cited

OTHER PUBLICATIONS

Qu, Y., et al., "Evolutionary Fuzzy Extreme Learning Machine for Mammographic Risk Analysis"; International Journal of Fuzzy Systems; vol. 13, No. 4, 2011, pp. 282-291.*
Heine, J.J., et al., "Full field digital mammography and breast density: comparison of calibrated and non-calibrated measurements," Acad Radiol, vol. 18, No. 11, 2011, pp. 1430-1436.
Martin, K.E., et al., "Mammographic Density Measured with Quantitative Computer-aided Method," Radiology, vol. 240, No. 3, 2006, pp. 656-662.
Qu, Y., et al., "Evolutionary Fuzzy Extreme Learning Machine for Mammographic Risk Analysis," International Journal of Fuzzy Systems, vol. 13, No. 4, 2011, pp. 282-291.
International Search Report and Written Opinion, dated Nov. 24, 2014, received in connection with International Patent Application No. PCT/US2014/040169.
International Preliminary Report on Patentability and Written Opinion, dated Dec. 1, 2015, received in connection with International Patent Application No. PCT/US2014/040169.

\* cited by examiner

METHOD OF ASSESSING BREAST DENSITY FOR BREAST CANCER RISK APPLICATIONS

STATEMENT REGARDING FEDERALLY SPONSORED RESEARCH OR DEVELOPMENT

This invention was made with Government Support under Grant No. CA114491 awarded by the National Institutes of Health. The Government has certain rights in the invention.

FIELD OF THE DISCLOSURE

This disclosure relates to a mammography; more specifically to methods of analyzing mammography results for estimating breast cancer risk for related applications such as for the detection of breast cancer.

BACKGROUND

Breast density is a significant breast cancer risk factor assessed from mammograms. Due to measurement difficulties and the lack of automation, breast density is used mainly for research purposes and not for breast cancer risk purposes in the clinical environment.

The Breast Imaging Reporting and Data Reporting System (BI-RADS) lexicon includes a breast tissue description for x-ray mammography. This categorization is a four-state ordinal scale comprised of a compact description of the overall breast composition accompanied with a percentage fibroglandular (glandular) tissue estimation as defined in the lexicon: [1] the breast is almost entirely fatty (<25% glandular); [2] there are scattered fibroglandular densities (approximately 25%-50% glandular); [3] the breast tissue is heterogeneously dense, which could obscure detection of small masses (approximately 51%-75% glandular); and [4] the breast is extremely dense. This may lower the sensitivity of mammography (>75% glandular). As indicated, these were developed to assess the reading difficulty of mammograms with ascending score for the patient's report. These ratings are dictated by the radiologist and may vary. In epidemiologic research, this set of descriptors has been extended beyond its original purpose to include breast cancer risk assessments. However, there lacks an automated measure of breast density to facilitate the related clinical applications.

SUMMARY

The present disclosure is directed to a calibration system for a specific full field digital mammography (FFDM) technology. The calibration adjusts for the x-ray acquisition technique differences across mammograms resulting in standardized images. The approach produced various calibrated and validated measures of breast density, one of which assesses variation in the mammogram referred to as Vc (i.e. variation measured from calibrated mammograms). The variation in raw mammograms [i.e. Vr] was a valid breast density risk factor in both FFDM in digitized film mammograms.

Below is presented a method of converting calibrated mammograms into a four-state ordinal variable as an approximation for the BI-RADS measurements using the histograms for each image. Also shown is how to covert the continuous variation measure of breast density into four-state ordinal variables as an approximation for the BI-RADS categories from both calibrated and raw FFDM images.

Additional features and advantages of the invention will be made apparent from the following detailed description of illustrative embodiments that proceeds with reference to the accompanying drawings. For example, in accordance with other aspects of the invention, the risk measure may include any combination of order measures discussed above.

BRIEF DESCRIPTION OF THE DRAWINGS

For a fuller understanding of the invention, reference should be made to the following detailed description, taken in connection with the accompanying drawings, in which.

DETAILED DESCRIPTION

Figure 1:
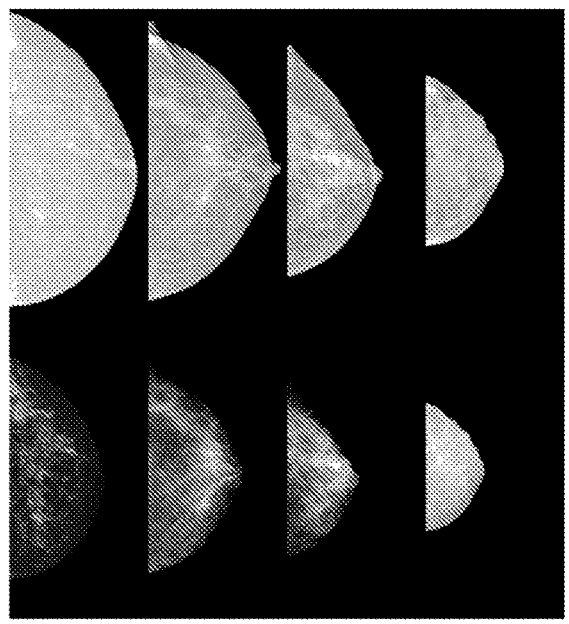
FIG. 1 illustrates example clinical-display images, which are used for viewing purposes as surrogates for the raw images.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The BI-RADS tissue composition descriptors were designed to rate mammogram reading difficulty as dictated by the radiologist. Subsequently, these ratings have been extended for breast cancer risk assessments. The present disclosure describes automated methods of converting both calibrated and raw mammograms into four-state ordinal variables as approximations for the BI-RADS tissue compositions using full field digital mammography (FFDM).

By way of introduction, a case-control dataset with FFDM images was used to investigate three approximations for the BI-RADS descriptors. Integrated histograms for each calibrated mammogram were used to create a four-state ordinal measure ($BR_{pg}$). Two previously validated variation measures of breast density derived from calibrated ($V_c$) and raw mammograms ($V_r$) were converted to four-state ordinal variables referred to as $BR_{vc}$ and $BR_{vr}$ respectively. The new measures were compared with the case-report BI-RADS (CR) distilled from the patient files.

Two optimization methods may be used to form the ordinal variables, where method-1 considered the case-control status, and method-2 matched the case-report findings. Differential evolution was used for the optimization analysis. Weighted kappa (κ) analysis was used to make comparisons of the new measures with the CR findings. Conditional logistic regression analysis was used to evaluate a given measure's association with breast cancer using odds ratios (ORs) with 95% confidence intervals.

Methods

Design Overview

For comparison purposes, the BI-RADS tissue composition assessments from the case-reports (i.e. from the patent records) were used as known quantities. For example, two approaches may be used to either develop or convert various continuous measures of breast density into four-state ordinal variables as approximations for the BI-RADS ratings: [1]

the case-control status may be considered as the endpoint comparison without considering the case-report BI-RADS, referred to as optimization method-1, and [2] the case-report BI-RADAS may be considered as the target quantities for the endpoint training and matching purposes, referred to as optimization method-2. These two approaches are similar but vary in the endpoint optimization fitness function. A Differential Evolution (DE) optimization technique may be used for both approaches. For optimization method-1, the cancer/no-cancer endpoint may be used to find the four-state ordinal variable from either the histograms of calibrated images or the continuous breast density variation measures (from calibrated and raw images) that provided the greatest association with breast cancer (i.e. case-control status discrimination and odds ratios). This goal may be achieved in combination with logistic regression (LR) modeling to find the parameters of the LR model and to find the four-state variable within a continual operation. For optimization method-2, the error may be minimized between the case-report BI-RADS and predicted BI-RADS category from a given measure without using logistic regression modeling or considering the breast cancer status endpoint.

Findings from calibrated mammograms are described below, as well as from the raw data representation. When calibrating a given mammogram, each pixel is mapped into the normalized percent glandular (PG) representation, making pixel quantities comparable across images. One BI-RADS measure was derived from the PG pixel representation by integrating (indefinite integral) the histogram for each image giving an approximation for the cumulative distribution. In this capacity the histogram is assuming the role of probability distribution function for a given image. The optimization finds critical/cutoff values (explained in detail below) using the cumulative distribution; this four-state variable is referred to as $BR_{pg}$. (BR is short for BI-RADS). Also, BI-RADS may be developed from the $V_c$ and $V_r$ measures. These BI-RADS approximations are referred to as $BR_{vc}$ and $BR_{vr}$, respectively.

Patient Population and Data

The patient population and data collection are surveyed below. This is a matched case-control population with images from FFDM. Cases are first-time unilateral breast cancer patients. Controls were individually matched to cases on age, hormone replacement therapy usage/duration, screening history, and breast laterality. All mammograms were acquired with one General Electric Senographe 2000D FFDM unit used for screening, located with the breast screening clinic at this facility. For a given patient, the image dataset includes the standard four screening mammograms. The analysis was restricted to cranial-caudal (CC) views.

The analysis was restricted to those patients that had the case-report BI-RADS available in their records. The BI-RADS ratings were available for 163 case-control pairs (163-dataset). Because the respective patients were selected over many years, these ratings were dictated by many radiologists and therefore have inherent inter-operator variability. This collection of BI-RADS assessments is referred to below as the case-report BI-RADS.

BI-RADS from Calibrated Pixels: $BR_{pg}$

The $BR_{pg}$ method uses the integrated histogram (i.e. cumulative distribution) from calibrated data. An arbitrary PG pixel value may e set to x and the normalized histogram set to p (probability distribution) for a given image. Although there are discrete pixel quantities, the cumulative distribution may defined using a continuous approximation for ease of notation and methodology description/development:

$$P(x) = \int_{x_{min}}^{x} p(x)\,dx.$$

When evaluating z=x, P(z) is the probability (or P) of x≤z. P(x) is found for every image and defined as $P_i(x)$, where the subscript, i, is the observation (i.e. the patient) index. When using either optimization method, four unknown parameters may be determined: $x_c$ which is the critical PG reference value and three P(x) function values given by q, r, and s. For an arbitrary observation, the four-state ordinal breast density measure, $BR_{pg}$, is determined by these four conditions:

$P_i(x_c) \geq q$, the sample is in group 1     (1)

$r \leq P_i(x_c) < q$, the sample is in group 2     (2)

$s \leq P_i(x_c) < r$, the sample is in group 3     (3)

$P_i(x_c) < s$, the sample is in group 4     (4)

The group designation parallels the BI-RADS class. For both optimization methods, the solution space was constrained such that s<r<q. When applying optimization method-1, DE may be used for two purposes within a sequence to find the parameter vector $p_v=[x_c, r, q, s]$ to estimate the four-state breast density variable. The four-state variable is then passed to the conditional LR modeling. DE is also used to find the LR coefficient vector $\beta=[\beta_0, \beta_1, \beta_2, \beta_3, \beta_4]$, where $\beta_0$ is the offset that factors out of the analysis in the matched case-control application, $\beta_1$ is the ordinal breast density measurement coefficient, $\beta_2$ is BMI coefficient, $\beta_3$ is the breast area coefficient, and $\beta_4$ is the binary menopausal status coefficient. In this approach, the area under the receiver operating characteristic curve (Az) may be estimated from the LR model output as the optimization's fitness function that drives the $p_v$ process. That is, the sequence is driven by attempting to increase Az. When optimization method-2 is applied, the problem is set up similarly (i.e. the four-state variable conditions cited above are the same) with a modified fitness function and without the simultaneous LR modeling. The predicted or estimated BI-RADS for the $i^{th}$ patient may be $BR_{pgi}$ (i.e. using $p_v$ components from the optimization procedure) and the case-report BI-RADS for the $i^{th}$ patient may be $BR_i$. The fitness function for optimization method-2 is defined as:

$$\Delta = \sum_{i=1}^{2n} |BR_i - BR_{pgi}|,$$

where n=100. The reason for using a 100 sample data subset is to prevent over-fitting, as discussed below. In this situation, the optimization is driven by minimizing Δ. In contrast with optimization method-1, the four-state variable is evaluated with LR after the optimization processes is terminated.

BI-RADS from the Variation Measures: $BR_{vc}$ and $BR_{vr}$

The variation measure can be calculated from either calibrated images or from the raw images i.e. giving $V_c$ and $V_r$, respectively. In either event, these are summaries measured from each breast calculated as the standard deviation of the pixel values within the eroded breast region. The breast region may be eroded to approximate the portion of the breast that was in contact with the compression paddle during the image acquisition as discussed previously (6, 9). For either $V_c$ or $V_r$, the optimization method finds three parameters defined as $p_v=[a, b, c]$ with a<b<c. These are cutoff values from the respective V distribution (describing the patient V distribution). The solution for this problem gives the four-state breast density variables $BR_{vc}$ and $BR_{vr}$, dependent upon using the calibrated or raw image variation measure as the process input. The respective four-state ordinal breast density measure for an arbitrary observation (i.e. using V generically) is determined from these four conditions:

$$V_i \leq a, \text{ the sample belongs to group 1} \quad (1)$$

$$a < V_i \leq b, \text{ the sample belongs to group 2} \quad (2)$$

$$b < V_i \leq c \text{ the sample belongs to group 3} \quad (3)$$

$$V_i > c, \text{ the sample belongs to group 4} \quad (4)$$

When applying either optimization method, the form is analogous to that of $BR_{pg}$ described above and therefore not repeated.

Optimization

Differential evolution (DE) optimization may be used to determine the parameter vectors defined above. For reference, the standard definitions for the DE parameters as provided by its founders ,au be used: the vector field population is NP=40 random vectors, the crossover is CR=0.1, and the evolutionary amplification factor was F=0.5. The maximum number of generations was fixed at G=1000. In brief, DE incrementally finds the parameters by either maximizing or minimizing the fitness function (whichever is applicable) by repeated processing of 100 image case-control (100 pair) dataset (the subset described below) with NP parameter-vector competitions at each generation to determine the vectors that form the next generation, where the process starts again. This process was initialized with 40 (i.e. NP) random vectors [uniformly distributed random variables over this range (0, 1)] for a given breast density measurement determination (i.e. $p_v$ as well as $\beta$ where applicable). The number of generations could terminate earlier than G=1000 when a preset convergence condition was met. For optimization method-1, the process was terminated early if $|Az_{maximum} - Az_{minimum}| \leq 0.01$ was reached within a given generation. For optimization method-2, the process was terminated early if $|\Delta_{maximum} - \Delta_{minimum}| \leq 0.001$ was reached within a given generation.

To introduce variation and mitigate over-training effects, each measure may developed by choosing random samples of 100 case-control pairs (bootstrap sub-datasets) from 163-dataset with replacement repeatedly as the inputs to the optimization process. For this process, cases were selected randomly (i.e. non-cancerous breast and an arbitrary breast side of their matched control was selected randomly. The final comparisons and analyses were based on the 163-dataset (i.e. non-cancerous breast with control breast-side matching).

Statistical Analyses

Conditional logistic regression may be used to assess a given measure's association with breast cancer. In the final analysis the non-cancerous breast side may be used for the cases and the matched side of the controls. Each BI-RADS measurement was treated as a four-state ordinal variable. The odds ratio (OR) findings are presented in both un-adjusted format and with simultaneous adjustments for body mass index (BMI) measured in kg/m$^2$, breast area (BA) measured in cm$^2$, and menopausal status (MS). All ORs are provided with 95% confidence intervals. The area under the receiver operating characteristic curve (Az) was used to assess a given model's ability to separate cases from controls.

The distribution for each of the new measures may be compared with the case-report BI-RADS assessments using a joint frequency analysis. To summarize the agreement (similarity/dissimilarity) and make comparisons, the weighted kappa statistic ($\kappa$) may e used due to ordinal nature of the measures. The value $\kappa$ may be used with 95% confidence intervals. The value of $\kappa$ may be between [−1, 1]. The upper $\kappa$ bound indicates perfect agreement between two distributions, zero indicates the distributions are disjoint, and the lower $\kappa$ bound indicates perfect negative agreement.

Results

Optimization

For optimization method-1, $x_c=23.0$ (PG units) and [q, r, s]≈[0.987, 0.700, 0.228] for the $BR_{pg}$ development. For illustration purposes, an explicit example is provided to describe the $BR_{pg}$ process. FIG. 1 (top) shows clinical-display images, which are used for viewing purposes as surrogates for the raw images, for patient samples corresponding to each of the BI-RADS categories (i.e. 1-4 from left to right). The bottom row shows the respective calibrated images after the erosion process.

Figure 2:
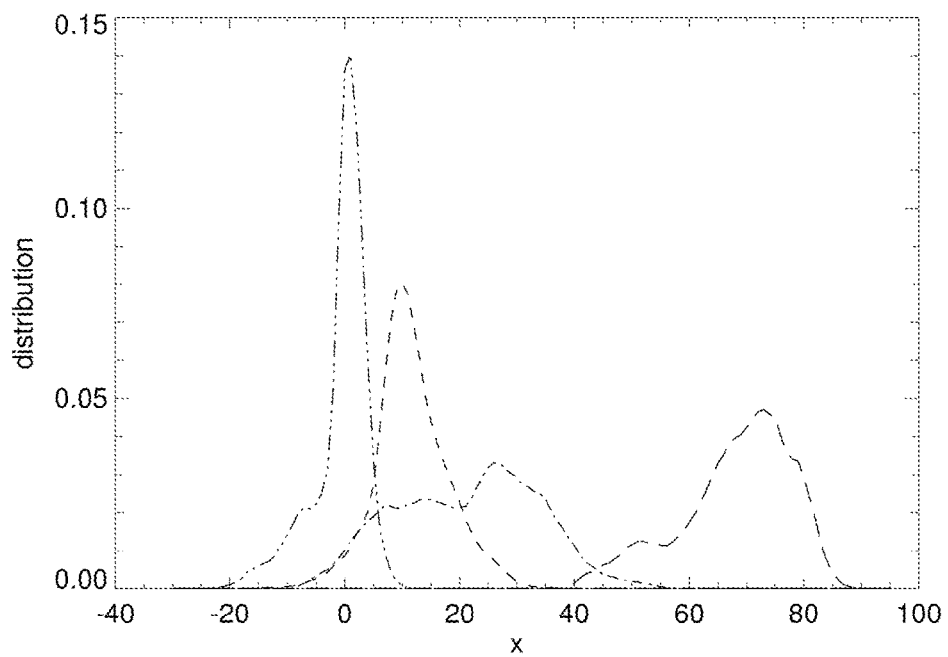
FIG. 2 shows example corresponding distributions, $p_i(x)$.
Figure 3:
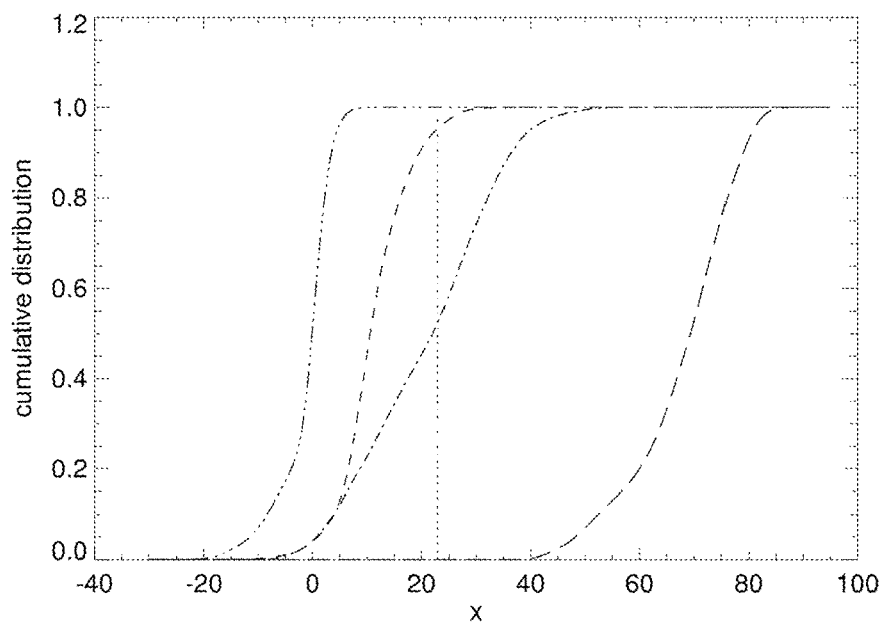
FIG. 3 shows the example corresponding cumulative distributions, $P_i(x)$, determined by integrating the distributions shown in FIG. 2.

FIG. 2 shows the corresponding distributions [i.e. $p_i(x)$]. FIG. 3 shows the corresponding cumulative distributions [i.e. $P_i(x)$] determined by integrating the distributions shown in FIG. 2 with $x_c$ denoted. This shows histograms from the four calibrated example mammograms shown in FIG. 1: [1] example 1 with long-dash and 3-dots; [2] example 2 with short-dash; [3] example 3 with dash-dot; and [4] example 4 with long-dash. The x-axis represents calibrated pixel values (x=percent glandular quantities). These histograms approximate the probability distributions for each image (vertical axis is the relative frequency). The $BR_{pg}$ process placed these images in the same categories as the case-report BI-RADS. The key to understating this measure in noting where $P_i(x_c=23)$ is situated with respect to (q, r, s) for a given patient. For example, the $p_i(x)$ and $P_i(x)$ examples defined by the long-dashes in FIG. 3 has $P_i(x_c)\approx 0.0$, indicating that 100% of its pixels within have values $>x_c$ and the image was placed in group 4. In contrast, the $P_i(x)$ defined by a long-dash and three-dots has $P_i(x_c)\approx 0.99$ indicating that 99% of its pixels have values less than $x_c=23$ and it was placed in group 1.

Also note in FIG. 2, in some situations x<0 in p(x), which theoretically should not exist. This may be due to both a mismatch in the adipose calibration phantom attenuation and that of adipose breast tissue and possibly inaccurate compressed breast height estimations as discussed previously (6, 9). For $BR_{vc}$, the following may be found [a, b, c]≈[4.8, 8.5, 14.5] and for $BR_{vr}$ found [a, b, c]≈[71.9, 151.1, 207.5]. The $BR_{vc}$ measure placed these examples in 1, 2, 3, and 3 categories respectively, whereas the $BR_{vr}$ measure placed them in 2, 2, 3, and 2 categories.

FIG. 3 shows the population distribution for $V_r$ and the [a, b, c] quantities marked with vertical dashes. The method for converting $V_c$ to the ordinal variable is analogous to that of converting $V_r$ and is, therefore, not shown (no examples provided). In FIG. 3, there is illustrated $BR_{pg}$ measure examples from optimization method-1. This shows the cumulative distributions determined from the histograms shown in FIG. 2. The $BR_{pg}$ processing with optimization method-1 categorized these examples as follows: [1] example 1 was placed in category 1 denoted with long-dash and 3-dots; [2] example 2 was placed in category 2 denoted with short-dash; [3] example 3 was placed in category 3 denoted with dash-dot; and [4] example 4 was placed in category 4 denoted with long-dash. The vertical line shows $x_c=23$.

For optimization method-2, the same interpretation follows as for method-1. For $BR_{pg}$, it was found that $x_c=19.0$ (PG units) and [q, r, s]≈[0.99, 0.98, 0.03]. The $BR_{pg}$ process placed the same examples in the 1, 3, 3, and 4 categories. For $BR_{vc}$ [a, b, c]≈[2.3, 5.7, 16.5] and the examples were placed in 2, 3, 3, and 3 categories. For $BR_{vr}$ [a, b, c]≈[32.0, 97.3, 326.1] and the examples were placed in the 2, 3, 3, and 3 categories (same as $BR_{vc}$). This similarity between the variation measures is expected because they are correlated. The differences between the findings crystallize when considering their associations with breast cancer.

Figure 4:
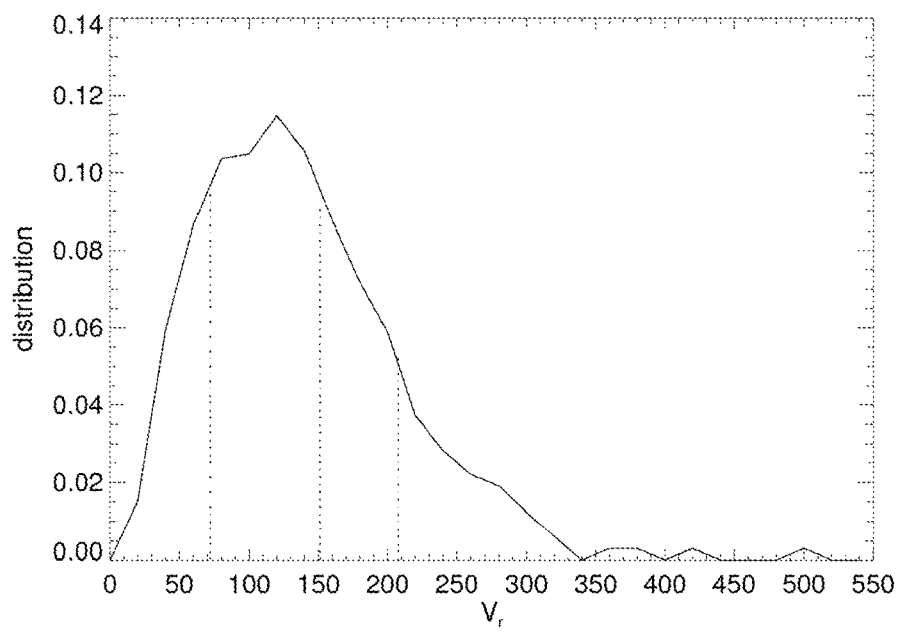
FIG. 4 illustrates an example $V_r$ population distribution, $BR_{vr}$ measurement and parameters from an example optimization method.

FIG. 4 illustrates the $V_r$ population distribution, $BR_{vr}$ measurement and parameters from optimization method-1. This shows the $V_r$ distribution for entire case-control dataset. The vertical lines (dashes) show the cutoff parameter values for the $BR_{vr}$ measure derived from optimization method-1 with [a, b, c]≈[71.9, 151.1, 207.5] from left to right corresponding to where the verticals lines (dashes) intersect the $V_r$ axis.

Breast Cancer Association

Table 1 provides the associations with breast cancer for the case-report BI-RADS (top) and for each new measure derived from optimization method-1 (left-side). In the adjusted models, the $BR_{pg}$ (OR=1.87; Az=0.648) and $BR_{vc}$ (OR=1.93; Az=0.663) calibrated measures provided significant OR associations and greater Az in comparison with the case-report BI-RADS (OR=1.49; Az=0.632), which showed the same trend but the OR was not significant. The $BR_{vr}$ findings (OR=1.37; Az=0.639) were similar to that of case-report BI-RADS associations (OR=1.49; Az=0.632), although the OR for $BR_{vr}$ was significant in the adjusted model. For easy comparison, the BI-RADS findings are also provided on the (top) right side of Table 2. For optimization method-2, the $BR_{pg}$ (OR=1.95; Az=0.634) and $BR_{vr}$ (OR=2.13; 0.639) findings provided significant ORs, whereas the $BR_{vc}$ (OR=1.42; Az=0.626) OR was not significant. There is an apparent fidelity reversal across the optimization methods.

TABLE 1

| | Optimization method-1 | | Optimization method-2 | |
| --- | --- | --- | --- | --- |
| BI-RADS Variable | OR per 1 unit increase unadjusted | OR per 1 unit increase adjusted (BMI, BA, MS) | BI-RADS Variable | OR per 1 unit increase unadjusted | OR per 1 unit increase adjusted (BMI, BA MS) |
| Case-report | 1.21 (0.85, 1.72) | 1.49 (0.99, 2.24) | Case-report | 1.21 (0.85, 1.72) | 1.49 (0.99, 2.24) |
| Az | 0.519 | 0.632 | Az | 0.519 | 0.632 |
| $BR_{pg}$ | 1.27 (0.99, 1.61) | 1.87 (1.34, 2.59) | $BR_{pg}$ | 1.26 (0.87, 1.82) | 1.95 (1.24, 3.09) |
| Az | 0.557 | 0.648 | Az | 0.527 | 0.634 |
| $BR_{vc}$ | 1.35 (1.03, 1.76) | 1.93 (1.36, 2.74) | $BR_{vc}$ | 1.10 (0.72, 1.70) | 1.42 (0.87, 2.32) |
| Az | 0.559 | 0.663 | Az | 0.51 | 0.626 |
| $BR_{vr}$ | 1.19 (0.94, 1.50) | 1.37 (1.05, 1.80) | $BR_{vr}$ | 1.50 (0.93, 2.42) | 2.13 (1.22, 3.72) |
| Az | 0.542 | 0.639 | Az | 0.538 | 0.639 |

TABLE 2

| | Case-report BI-RADS | | | | |
| --- | --- | --- | --- | --- | --- |
| $BR_{pg}$ | 1 | 2 | 3 | 4 | n |
| 1 | 5 | 60 | 38 | 1 | 104 |
| 2 | 1 | 27 | 73 | 5 | 106 |
| 3 | 0 | 9 | 50 | 11 | 70 |
| 4 | 0 | 3 | 21 | 22 | 46 |
| n | 6 | 99 | 182 | 39 | 326 |

κ: 0.25 (0.19, 0.31)

| | Case-report BI-RADS | | | | |
| --- | --- | --- | --- | --- | --- |
| $BR_{vc}$ | 1 | 2 | 3 | 4 | n |
| 1 | 6 | 38 | 9 | 0 | 53 |
| 2 | 0 | 42 | 70 | 4 | 116 |
| 3 | 0 | 18 | 86 | 19 | 123 |
| 4 | 0 | 1 | 17 | 16 | 34 |
| n | 6 | 99 | 182 | 39 | 326 |

κ: 0.34 (0.27, 0.41)

| | Case-report BI-RADS | | | | |
| --- | --- | --- | --- | --- | --- |
| $BR_{vr}$ | 1 | 2 | 3 | 4 | n |
| 1 | 5 | 35 | 11 | 1 | 52 |
| 2 | 1 | 47 | 78 | 13 | 139 |
| 3 | 0 | 12 | 63 | 7 | 82 |
| 4 | 0 | 5 | 30 | 18 | 53 |
| n | 6 | 99 | 182 | 39 | 326 |

κ: 0.27 (0.21, 0.34)

In summary, $BR_{pg}$ from optimization method-1 provided the greater predictive capability when considering all measurements across both optimizations methods, but within optimization method-2, both $BR_{pg}$ and $BR_{vr}$ were approximately equivalent and provided the larger predictive capability. These findings can be qualified further after considering the joint distribution and κ analyses. The new measures all compared well against the associations and Az provided by the case-report BI-RADS assessments.

Joint Frequency Analysis

The weighted κ analysis was used to assess the joint distribution of any two measurements and make comparisons. The findings from optimization method-1 for each of the four-state variables compared with the case-report BI-RADS assessments are provided in Table 2 with percentages provided in the caption. All three measures are related to the case-report measure with κ=0.25 for $BR_{pg}$, κ=0.34 for $BR_{vc}$, and, κ=0.27 for $BR_{vr}$. The $BR_{vc}$ measure provided the closest agreement with the case-report measure. There are relatively few case-report observations in the first category (n=6) and many in the third category (n=182). In contrast, the other measures tended to spread the placements across the categories more generally due to the optimization fitness function. The corresponding findings for optimization method-2 are shown in Table 3. All measures provided similar agreement with the case-report BI-RADS with κ=0.42 for $BR_{pg}$, κ=0.45 for $BR_{vc}$, and, κ=0.42 for $BR_{vr}$. In contrast with optimization method-1, the automated measures tend to localize the placements into the second and third categories due to the error based fitness function, which attempts to match the case-report placements.

TABLE 3

| | Case-report BI-RADS | | | | |
|---|---|---|---|---|---|
| $BR_{pg}$ | 1 | 2 | 3 | 4 | n |
| 1 | 2 | 9 | 3 | 0 | 14 |
| 2 | 3 | 38 | 20 | 0 | 61 |
| 3 | 1 | 51 | 150 | 21 | 223 |
| 4 | 0 | 1 | 9 | 18 | 28 |
| n | 6 | 99 | 182 | 39 | 326 |

κ: 0.42 (0.33, 0.50)

| | Case-report BI-RADS | | | | |
|---|---|---|---|---|---|
| $BR_{vc}$ | 1 | 2 | 3 | 4 | n |
| 1 | 1 | 0 | 0 | 0 | 1 |
| 2 | 5 | 56 | 23 | 1 | 85 |
| 3 | 0 | 42 | 155 | 28 | 225 |
| 4 | 0 | 1 | 4 | 10 | 15 |
| n | 6 | 99 | 182 | 39 | 326 |

κ: 0.45 (0.37, 0.54)

| | Case-report BI-RADS | | | | |
|---|---|---|---|---|---|
| $BR_{vr}$ | 1 | 2 | 3 | 4 | n |
| 1 | 0 | 0 | 0 | 0 | 0 |
| 2 | 6 | 61 | 24 | 2 | 93 |
| 3 | 0 | 37 | 157 | 34 | 228 |
| 4 | 0 | 1 | 1 | 3 | 5 |
| n | 6 | 99 | 182 | 39 | 326 |

κ: 0.42 (0.34, 0.50)

Discussion

Two methods were presented for approximating the BI-RADS measurements. One approach used validated breast density measurements and their population distributions to find cutoff values for the four-state ordinal variable conversion. The other approach used the integrated histogram, or cumulative distribution, for each calibrated image to estimate the four-states. The first method can apply to any continuous measure of breast density, with or without calibration, as demonstrated with $V_r$ and $V_c$. The cumulative distribution approach applies to calibrated data only and illustrates a benefit of establishing a calibration system. DE was used for the optimization task and applied it with two different endpoints or fitness functions. Optimization method-1 does not require a priori BI-RADS assessments for the endpoint comparisons to develop the ordinal measure making it a desirable approach, in particular when case-report findings are not available. The BI-RADS assessments from an operator tend to provide a measure of increasing breast cancer risk with increasing category but with some ambiguity in the lower categories. Essentially, optimization approach-1 creates a measure with the characteristics of the BI-RADS percentages definition in that there is increasing risk with increasing breast density for each category, as dictated by the logistic regression modeling process in its development. In contrast, optimization method-2 requires existing BI-RADS assessments for endpoint matching purposes. As demonstrated, optimization methods-2 provides closer agreement with the case-report BI-RADS, whereas the other optimization method produces stronger predictive capability. When noting the κ statistic for each of the experimental measures, and comparing the ORs and Az quantities with the case-report BI-RADS, it is concluded that all new measures are at least equivalent with the case-report measures. The strength of the present methodology is that no assumptions are required within its framework other than the four-state variable imposition, which can also be modified easily. Moreover, the fitness function can be modified easily as demonstrated.

In the above, the measures were developed with a limited dataset. Related work in FFDM shows that the BI-RADS percentages are 9.5%, 45.6%, 35.3%, and 9.6% for the first through fourth categories, respectively, as estimates from a relatively large population. The $BR_{vc}$ provided (see caption Table 2) the closest agreement (optimization method-1) with this related work when considering the percentages, i.e. $BR_{vc}$ gave 16.3%, 35.6%, 37.7%, and 10.4%, respectively. Randomness was used in the training to mitigate over-fitting. Because only a few partners were estimated, over-fitting is probably not a limitation but validation on independent datasets is still required.

The BI-RADS composition descriptors include percentages as well as a verbal description related to texture. Two forms of measurements were used that are almost disjoint. The integrated histogram approach is related to the breast density content but does not include variation or a texture component. In contrast, the variation measures capture a broad range of texture information but not the degree, or amount, of dense breast tissue explicitly. Optimization method-1 does not consider these percentages explicitly. In contrast, optimization method-2 considers these percentages as they are captured by the radiologists reporting. Future work includes combining these measures as to capture the degree of breast density and the texture components simultaneously. The most appropriate method will require more analysis.

CONCLUSION

Thus, described above is a general methodology for converting continuous measurements of breast density and calibrated mammograms into a four-state ordinal variable approximating the BI-RADS ratings. The disclosure demonstrates the benefits of developing a calibration methodology. The disclosure also shows calibration is not required, which may be important when establishing a calibration system is not possible. The disclosure was validated with a preliminary dataset and will require further analysis to establish its generality.

The present disclosure references one or more publications. Each of the references in the present disclosure is incorporated herein by reference in its entirety. In addition, in the above, all measures and combinations of measures may include solely raw data or calibrated data, as well as a mixture of raw and calibrated measures.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

What is claimed is:

1. A method of assessing breast density for breast cancer risk applications, the method comprising:
receiving digital image data including a plurality of pixels;
calibrating the digital image data, wherein each pixel is mapped into a normalized percent glandular representation;
performing a statistical analysis with optimization on the calibrated digital image data, by;
determining measured characteristics of the calibrated image or the digital image data based on a deviation of the pixel values within a breast region; and
determining four-state breast density variables based on the determined measured characteristics by applying an optimization, wherein the optimization comprises maximizing or minimizing a fitness function by a repeated processing of case-control data with plural random vectors for a given breast density measurement determination for a number of generations, wherein the number of generations is less than predetermined value when a preset convergence condition is met; and
associating the statistically analyzed digital image data with a measure of risk for breast cancer.

2. The method of claim 1, wherein the present convergence condition is met when $|AZ_{Maximum}-AZ_{Minimum}| \leq 0.01$ in a given generation.

3. The method of claim 2, further comprising:
generating an integrated histogram from the calibrated data;
performing a statistical analysis with optimization on the generated integrated histogram; and
determining four-state breast density variables based on the analyzed integrated histogram data with a measure of risk for breast cancer.

4. The method of claim 3, further comprising comparing the four state breast density variables based on the integrated histogram with the four state breast density variables based on the determined characteristics.

5. The method of claim 1, wherein the present convergence condition is met when $|\Delta_{Maximum}-\Delta_{minimum}| \leq 0.001$ in a given generation.

6. The method of claim 5, further comprising:
generating an integrated histogram from the calibrated data;
performing a statistical analysis with optimization on the generated integrated histogram; and
determining four-state breast density variables based on the analyzed integrated histogram data with a measure of risk for breast cancer.

7. The method of claim 6, further comprising comparing the four state breast density variables based on the integrated histogram with the four state breast density variables based on the determined characteristics.

8. The method of claim 1, wherein the measured characteristics include a measured variation.

9. The method of claim 1, wherein the optimization is a differential evolution optimization.

10. A method of assessing breast density for breast cancer risk applications, the method comprising:
receiving digital image data including a plurality of pixels;
performing a statistical analysis with optimization on the calibrated digital image data or the digital image data;
determining measured characteristics of the received image based on a deviation of the pixel values within a breast region;
determining four-state breast density variables based on the determined measured characteristics by applying an optimization that comprises maximizing or minimizing a fitness function by a repeated processing of image case-control datasets with plural random vectors for a given breast density measurement determination for a number of generations, wherein the number of generations is less than a predetermined value when a preset convergence condition is met; and
associating the statistically analyzed digital image data with a measure of risk for breast cancer.

11. The method of claim 10, wherein the present convergence condition is met when $|AZ_{Maximum}-AZ_{minimum}| \leq 0.01$ in a given generation.

12. The method of claim 11, further comprising:
generating an integrated histogram from the calibrated data;
performing a statistical analysis with optimization on the generated integrated histogram; and
determining four-state breast density variables based on the analyzed integrated histogram data with a measure of risk for breast cancer.

13. The method of claim 12, further comprising comparing the four state breast density variables based on the integrated histogram with the four state breast density variables based on the determined measured characteristics.

14. The method of claim 10, wherein the present convergence condition is met when $|\Delta_{Maximum}-\Delta_{Minimum}| \leq 0.001$ in a given generation.

15. The method of claim 14, further comprising:
generating an integrated histogram from the calibrated data;
performing a statistical analysis with optimization on the generated integrated histogram; and
determining four-state breast density variables based on the analyzed integrated histogram data with a measure of risk for breast cancer.

16. The method of claim 15, further comprising comparing the four state breast density variables based on the integrated histogram with the four state breast density variables based on the determined measured characteristics.

17. The method of claim 10, wherein the measured characteristics include a measured variation.

18. The method of claim 10, wherein the optimization is a differential evolution optimization.

\* \* \* \* \*